(12) United States Patent
Autiero et al.

(10) Patent No.: US 7,087,384 B2
(45) Date of Patent: Aug. 8, 2006

(54) RARE EARTH METAL CRYPTATES WHICH ARE NOT VERY SENSITIVE TO THE FLUORESCENCE QUENCHING

(75) Inventors: Herve Autiero, Villeneuve Les Avignon (FR); Herve Bazin, Villeneuve Les Avignon (FR); Gerard Mathis, Bagnols Sur Ceze (FR)

(73) Assignee: CIS bio international, Saclay (FR)

( * ) Notice: Subject to any disclaimer, the term of this patent is extended or adjusted under 35 U.S.C. 154(b) by 585 days.

(21) Appl. No.: 10/311,534

(22) PCT Filed: Jun. 12, 2001

(86) PCT No.: PCT/EP01/06642

§ 371 (c)(1),
(2), (4) Date: Dec. 16, 2002

(87) PCT Pub. No.: WO01/96877

PCT Pub. Date: Dec. 20, 2001

(65) Prior Publication Data

US 2004/0092726 A1    May 13, 2004

(30) Foreign Application Priority Data

Jun. 15, 2000   (FR) .................................. 00 07650

(51) Int. Cl.
| | |
|---|---|
| *C12Q 1/68* | (2006.01) |
| *C07H 21/04* | (2006.01) |
| *C07H 19/04* | (2006.01) |
| *C07F 5/00* | (2006.01) |
| *C07D 225/00* | (2006.01) |

(52) U.S. Cl. ...................... 435/6; 536/23.1; 536/26.6; 540/452; 540/469; 540/472; 534/15

(58) Field of Classification Search .................... 435/6; 536/23.1, 26.6; 540/452, 469, 472; 534/15
See application file for complete search history.

(56) References Cited

U.S. PATENT DOCUMENTS 5,696,240 A   12/1997 Vallarino et al.
5,925,744 A    7/1999 Haener et al.

FOREIGN PATENT DOCUMENTS

WO       WO 99 18114 A      4/1999

OTHER PUBLICATIONS

G. Mathis: "Rare Earth Cryptates and Homogeneous Fluoroimmunoassays with Human Sera"; Clinical Chemistry, US, American Association for Clinical Chemistry; Winston; vol. 39, No. 9, 1993, pp. 1953-1959, XP002125039; ISSN: 0009-9147.
E. Lopez et al.: "Europium (III) Trisbipyridine Cryptate Label for the Time-Resolved Fluorescence Detection of Polymerase Chain Reaction Products Fixed on a Solid Support"; Clinical Chemistry, US, American Association for Clinical Chemistry; Winston, vol. 39, No. 2, 1993, pp. 196-201, XP002125037; ISSN: 0009-9147; p. 197; Figure 1.
Beatrice Alpha; Elke Anklam; Robert Deschenaux; Jean-Marie Lehn; Marek Pietraskiewicz: "Synthesis and Characterization of the Sodium and Lithium Cryptates of Macrobicyclic Ligands Incorporating Pyridine, Bipyridine, and Biisoquinoline Units"; Helv. Chim. Acta, vol. 71, 1988, pp. 1042-1052; XP002165652.

*Primary Examiner*—Jezia Riley
(74) *Attorney, Agent, or Firm*—Millen, White, Zelano & Branigan, P.C.

(57) ABSTRACT

The invention relates to a process for reducing the fluorescence quenching caused by the measuring medium in a fluorescence assay, by introducing into said medium of rare earth metal cryptates which are not very sensitive to this fluorescence quenching, said rare earth metal cryptates comprising at least one pyridine radical which is substituted one or more times or unsubstituted.

The invention also relates to novel rare earth metal cryptates which are not very sensitive to the fluorescence quenching caused by the measuring medium.

22 Claims, No Drawings

RARE EARTH METAL CRYPTATES WHICH ARE NOT VERY SENSITIVE TO THE FLUORESCENCE QUENCHING

The invention relates to a process for reducing the fluorescence quenching caused by the measuring medium in a fluorescence assay, by introducing into said medium rare earth metal cryptates which are not very sensitive to this fluorescence quenching.

The invention also relates to novel rare earth metal cryptates which are not very sensitive to the fluorescence quenching caused by the measuring medium.

The advancement of knowledge in biology is creating an increasing need for diagnostic methods enabling biomolecules to be monitored or quantified.

At the same time, there is disaffection toward the radioactive labels which are generally involved in reference assay methods. In general, efforts are currently directed toward replacing radioactive tracers with other labels and mainly with fluorescent labels. The use of fluorescent labels under ideal conditions makes it possible to obtain high sensitivities that are theoretically equivalent to those obtained with radioactive tracers.

Many fluorescent molecules which may be used as tracers in assays of this type have previously been described, among which rare earth metal complexes have advantageous properties.

The use of particular complexes, rare earth metal cryptates, is disclosed for example in patent applications EP 0 180 492 and EP 0 321 353.

In practice, the performance qualities of fluorescent tracers are limited firstly by the presence of a background noise which is often high, and secondly by the fact that they are generally very sensitive to changes in their environment. Small changes in the pH, the polarity, the presence of dissolved oxygen or the proximity of heavy atoms (for example iodine) or absorbing groups can modify their quantum yield (in the sense of an excitement or a quenching) or shift the emission wavelength.

The problems inherent in the methods of analysis by measuring the fluorescence are listed in a review article (I. Hemmilä, Clin. Chem. 31/3, 359–370 (1985)).

The problems inherent in the background noise arising from the intrinsic fluorescence of proteins and also of other biomolecules present in biological samples may be partially solved by using fluorescent labels formed from of rare earth metal complexes (mainly europium) which allow a temporal selection of the specific signal. The particularly long lifetimes (0.1 ms to 1 ms approximately) which characterize europium complexes make it possible, by means of a resolved-time measurement, to be free of the background noise arising, for example, from the serum proteins, this noise being characterized by a relatively short lifetime (about 4 ns).

A format of homogeneous type has the considerable advantage of allowing real-time monitoring of the kinetics of formation of an immunological complex, but does not, however, make it possible to be free of any unfavorable interactions between the label and the molecules present in a biological medium (quenching of the fluorescence).

A restoration of the photophysical properties, and in particular the lifetime, may be obtained in a serum medium by adding fluoride ions to the medium, as disclosed in the patent application EP 0 539 435.

Nevertheless, the problems of interference caused by the molecules present in the measuring medium are not fully solved by any of these methods. The reason for this is that a major cause of limitation of the sensitivity of the measurement by fluorescence is the existence of quenching processes caused by molecules present in the medium which are capable of inhibiting the fluorescence of the fluorescent molecule used as label in the assay. In the case of rare earth metal complexes, the quenching may be the result of mechanisms of electron transfer by proximity, in which the inhibitor molecule occupies the free coordination sites in the complex. Mention may be made in particular of the redox reactions taking place between the fluorescent molecule in its ground state or in its excited state and molecules present in the medium. These mechanisms are capable of appreciably modifying the emitted fluorescence.

The inhibition of fluorescence by mechanisms involving electron transfer and in general by quenching mechanisms is a severe indisposition in practice since the inhibitory factors may either be naturally present as components in the measuring medium (for example uric acid in serum) or else be added thereto as additives or stabilizers for the assay.

These inhibitors greatly impair the fluorescence of the label molecule. In particular, in the case of interfering redox reactions, passage from the oxidized state to the reduced state of a rare earth metal ion by means of a redox mechanism entails a reduction in the lifetime and a change in the emission spectrum of the complex containing it, such that the sensitivity of the measurement is greatly impaired.

Novel rare earth metal cryptates consisting of a rare earth metal salt complexed with a macropolycyclic compound comprising at least one molecular unit consisting of a pyridine have now been found, and show novel and unexpected photophysical properties.

It has also been found that these advantageous properties are observed when this macropolycyclic compound also comprises a molecular unit having a triplet energy which is higher than that of the emission level of the complexed rare earth metal ion which is substituted with an electron-donating group.

One mechanistic hypothesis in this regard is that the replacement of a molecular unit of greater steric bulk with a pyridine reduces the cavity of the macrocycle and has an influence on the redox equilibrium of the rare earth metal ion by promoting its oxidized state.

The presence of an electron-donating group is also capable of influencing the redox potential of the rare earth metal ion.

The rare earth metal cryptates according to the invention thus have the advantageous property of being less sensitive, compared with corresponding cryptates not comprising a pyridine unit and/or a substitution with an electron-donating group, to the phenomenon of fluorescence quenching resulting from an interaction with molecules present in the medium.

This observation is of great interest since it enables fluorescence measurements to be performed in biological media without using an adjuvant such as fluoride ions.

The compounds according to the invention thus constitute novel labels, which may be coupled to a biological molecule having a recognition role and which may bind to a partner, while at the same time retaining their quenching-resistance properties.

According to a first aspect, the invention thus relates to a process for reducing the fluorescence quenching caused by the measuring medium in a fluorescence assay of an analyte using at least one fluorescent label, characterized in that a rare earth metal macropolycyclic complex is introduced into the measuring medium, this complex consisting of at least one rare earth metal salt complexed with a macropolycyclic compound of formula

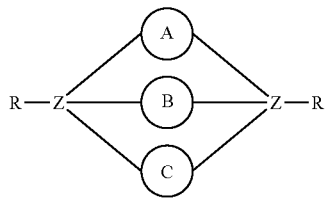

I in which Z is an atom with 3 or 4 valencies, H is nothing or represents hydrogen, a hydroxyl group, an amino group or a hydrocarbon radical, the divalent radicals Ⓐ, Ⓑ and Ⓒ are, independently of each other, hydrocarbon chains optionally containing one or more hetero atoms and are optionally interrupted with a hetero macrocycle, at least one of the radicals Ⓐ, Ⓑ and Ⓒ also comprising at least one molecular unit or consisting essentially of a molecular unit having a triplet energy which is greater than that of the emission level of the complexed rare earth metal ion, and at least one of the radicals Ⓐ, Ⓑ and Ⓒ which does not comprise or does not consist essentially of said molecular unit comprises a pyridine radical which is substituted one or more times or unsubstituted.

When the macropolycyclic compound of formula (I) comprises a substituted pyridine radical, it may be substituted with one or more substituents, which may be identical or different, such as, for example, halogen, CN, $C_1$–$C_6$ carboxylic ester, OH, $NH_2$, $NO_2$, —$CH_2$NHCONH-aryl, —$CH_2$NHCSNH-aryl, —NHCONH—($C_1$–$C_6$)alkyl, —NHCSNH—($C_1$–$C_4$)alkyl, —NHCONH-aryl, —NHCSNH-aryl, piperidyl, —N—($C_{1-6}$)alkyl-carboxypyperidyl, ($C_1$–$C_4$)alkylamino-alkylamine, $C_1$–$C_{10}$ alkyl, alkenyl containing 2 to 10 carbon atoms, alkynyl containing 2 to 10 carbon atoms, cycloalkyl containing 3 to 8 carbon atoms, hydroxyalkyl containing 1 to 5 carbon atoms, alkoxy containing 1 to 10 carbon atoms, alkoxyalkyl containing 2 to 10 carbon atoms, alkoxyalkoxyalkyl containing 3 to 10 carbon atoms, alkoxyalkoxy containing 2 to 10 carbon atoms, alkenyloxy containing 2 to 10 carbon atoms, alkylthio containing 1 to 10 carbon atoms, alkylthioalkyl containing 2 to 10 carbon atoms, acylamino containing 1 to 7 carbon atoms, acylaminoalkyl containing 2 to 8 carbon atoms, carbamoylalkyl containing 2 to 5 carbon atoms, alkylaminocarbonylalkyl containing 3 to 9 carbon atoms, amino ($C_1$–$C_6$)alkyl, amino($C_1$–$C_6$)alkylcarboxamide, amino($C_1$–$C_6$)alkylcarboxamido($C_1$–$C_6$)alkyl and carboxy ($C_1$–$C_{10}$)alkyl.

Preferably, a substituted pyridine will comprise one or 2 substituents. Substituents that are preferred for the purposes of the invention are, for example, the following substituents: amino($C_1$–$C_6$)alkyl, in particular aminomethyl or aminoethyl; amino($C_1$–$C_6$)alkylcarboxamide, in particular aminoethylcarboxamide, phenylcarbamoyl; phenylthiocarbamoyl; nitrile; piperidyl; $C_1$–$C_6$ carboxylic ester, in particular methylcarboxylate or ethylcarboxylate; amino($C_1$–$C_6$)alkylcarboxamido($C_1$–$C_6$)alkyl, in particular aminocaproylamidomethyl and aminocaproylamidoethyl or carboxy ($C_1$–$C_{10}$) alkyl.

In the present description, the term "analyte" means any substance or group of substances, as well as analogs thereof, which it is desired to detect and/or determine.

According to one preferred aspect of the process according to the invention, the two radicals Ⓐ, Ⓑ or Ⓒ which do not comprise or do not consist essentially of a molecular unit having a triplet energy which is greater than that of the emission level of the complexed rare earth metal ion comprise a substituted or unsubstituted pyridine radical.

Advantageously, the molecular unit having a triplet energy which is greater than that of the emission level of the complexed rare earth metal ion is substituted with an electron-donating group.

Preferably, the molecular unit having a triplet energy which is greater than that of the emission level of the complexed rare earth metal ion is chosen from phenanthroline, anthracene, benzene, naphthalene, biphenyl, terphenyl, azobenzene, azopyridine, bipyridines and bisisoquinolines, bipyridines being preferred.

According to another preferred aspect of the process according to the invention, the bypiridine unit(s) is (are) substituted with an electron-donating group chosen in particular from the following groups: carboxylate, —$NH_2$, —NHAlk, —N(Alk)$_2$, OH, O$^-$, —OAlk, Alk, —CH(Alk)$_2$, —C(Alk)$_3$, —NHCOAlk, substituted or unsubstituted phenyl; Alk being a ($C_1$–$C_4$)alkyl group.

When the phenyl is substituted, it may be substituted with one or more substituents, which may be identical or different, chosen, for example, from sulfonate, carboxylate, methylcarboxylate, N,N-dimethylamino, methoxyethylcarboxylate and carboxamide.

The carboxylate group is an electron-donating group which is particularly preferred for the purposes of the invention.

The term "carboxylate group" means the —COOH/—COO$^-$ couple: specifically, the macrocyclic complex may comprise during its synthesis a carboxylic acid group —COOH, this group being ionized, during its use in the measuring medium, to a carboxylate group —COO$^-$.

According to one advantageous aspect of the process according to the invention, the macropolycyclic compound is composed of at least one rare earth metal salt complexed with a macrocylic compound corresponding to formula (II) below:

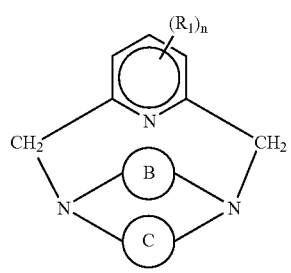

II in which:
  the ring of formula

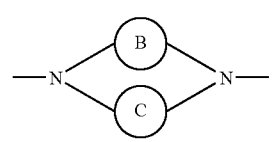

is the bis-bipyridine macrocycle of formula:

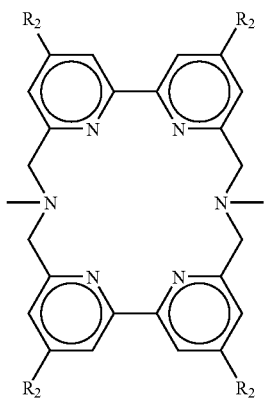

n=0, 1 or 2;

A is a functional group capable of bonding covalently with a biological substance;

$R_1$ is a group —COOR$_3$ in which $R_3$ is hydrogen or a $C_1$ to $C_{10}$ alkyl group and preferably represents a methyl, ethyl or tert-butyl group or $R_1$ is a group —CO—NH—Y-A or —Y-A;

$R_2$ is hydrogen, an electron-donating group, in particular carboxylate, —NH$_2$, —NHAlk, —N(Alk)$_2$, OH, O⁻, —OAlk, Alk, —CH(Alk)$_2$, —C(Alk)$_3$, —NHCOAlk, substituted or unsubstituted phenyl; Alk being a (C$_1$–C$_4$)alkyl group or a group —CO—NH—Y-A or —Y-A, with the proviso that not more than one of the substituents $R_1$ and $R_2$ represents a group —CO—NH—Y-A or —Y-A and $R_1$ and $R_2$ do not simultaneously represent a group —CO—NH—YA or —Y-A;

Y is a spacer group or spacer arm which consists of a divalent organic radical, chosen from linear or branched $C_1$ to $C_{20}$ alkylene groups optionally containing one or more double bonds and/or one or more heteroatoms such as oxygen, nitrogen, sulfur or phosphorus or one or more carbamoyl or carboxamido group(s); or else chosen from $C_5$ to $C_8$ cycloalkylene groups or from $C_6$ to $C_{14}$ arylene groups, said alkylene, cycloalkylene or arylene groups being optionally substituted with alkyl, aryl or sulfonate groups.

In the present description, the expression "functional group capable of bonding covalently with a biological substance" denotes any functional group capable of bonding via a covalent bond, directly or after activation with at least one of the functions naturally present or artificially introduced into said biological substance. Such functions are, in particular, NH$_2$, COOH, SH and OH functions. Such groups and the activation processes are described in detail by P. Tijssen in "Practice and Theory of Enzyme immunoassays" Elsevier 1985.

As examples of functional groups that are suitable for the purposes of the invention, mention may be made in particular of amino, thio, cyano, isocyano, isothiocyano, thiocyano, carboxyl, hydroxyl, maleimido, succinimido, mercapto, phenol, imidazole, aldehyde, epoxide, halogen, thionyl, sulfonyl, nitrobenzyl, carbonyl, triazo, anhydride, haloacetate, hydrazino, acridine, etc. groups.

The groups that are particularly preferred are amino, thiol and carboxyl groups, which must be activated before the covalent coupling with the biological substance, and also maleimido, succinimido and isothiocyanate groups, which can bond directly with the biological substance.

The complexed rare earth metal ion is preferably a europium ion.

In the present description, the "cryptate" notion and the nomenclature of the macrocycles and polycycles are as defined by J. M. Lehn in Struct. Bonding (Berlin), 16, 1, 1973 and in Acc. Chem. Res. 11, 49, (1978).

The following abbreviations have been used to denote the constituent molecular units of the macro(poly)cycles:

2,2'-bipyridine=bpy pyridine=Py 4-methylisonicotinate=Py(CO$_2$Me)

2,2'-bipyridine-4,4'-diethylcarboxylate=bpy(CO$_2$Et)$_2$ 2,2'-bipyridine-4,4'-di-tert-butylcarboxylate=bpy(CO$_2$tbu)$_2$ 2,2'-bipyridine-4,4'-dicarboxylic acid=bpy(CO$_2$H)$_2$ pyridine-3,5-diethylcarboxylate=Py(CO$_2$Et)$_2$ 3,5-bis[N-(2-aminoethyl)carboxamidyl]pyridine=Py(NH$_2$)$_2$ 3,5-bis[N-(4-maleimidomethylcyclohexylcarboxamido-2-ethyl)carboxamidyl]pyridine=Py[CONH(CH$_2$)$_2$NHR$_4$]$_2$, in which

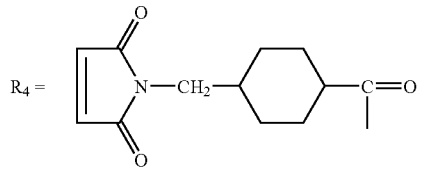

The rare earth metal macropolycyclic complexes that are particularly preferred for the purposes of the invention are the europium cryptates [Eu$^{3+}$⊂py.Bpy(CO$_2$H)$_2$.Bpy(CO$_2$H)$_2$] (Example 4, b), [Eu$^{3+}$⊂bpy(CO$_2$H)$_2$.bpy(CO$_2$H)$_2$.py(NH$_2$)$_2$] (Example 6) and [Eu$^{3+}$⊂bpy(CO$_2$H)$_2$.bpy(CO$_2$H)$_2$.py(CONH(CH$_2$)$_2$NHR$_4$]$_2$ in which

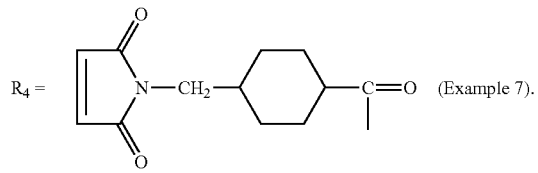

(Example 7).

According to one preferred aspect of the process according to the invention, the rare earth metal macrocyclic complex is used as sole label or as one of the labels in the assay.

Advantageously, the measuring medium is a biological medium, in particular a serum medium.

The macro(poly)cyclic compounds which may be used in the process according to the invention are prepared according to known processes. The preparation of the bipyridine macrocycle passing via a tosyl intermediate is described in particular in J. Org. Chem. 1983, 48, 4848; the functionalized macrocyclic analogs of bpy.bpy.(R$_2$)$_2$ type were obtained by the same approach.

In general, the macrobicyclic ligands are prepared according to the techniques disclosed, respectively, in patent EP 0 321 353 and in Helv. Chim. Acta, 1988, 71, 1042. In particular, these molecules were prepared by alkylating a macrocyclic diamine preformed in a polar aprotic solvent in the presence of an alkaline carbonate acting as base and template ion.

The rare earth metal macropolycyclic complexes which may be used according to the invention may be obtained by the conventional processes for preparing metal complexes, which consist in reacting the complexing compound with a compound which donates the cation to be complexed.

For example, the macropolycyclic complexes may be obtained by reacting a compound which donates a rare earth metal cation with the macropolycyclic compound having the characteristics defined above, each compound advantageously being in solution, preferably in the same solvent or in compatible solvents that are inert with respect to the complexation. In general, acetonitrile or methanol is used as solvent, with heating to reflux.

According to a further aspect, the invention also relates to rare earth metal macropolycyclic complexes, consisting of at least one rare earth metal salt complexed with a macropolycyclic compound of formula

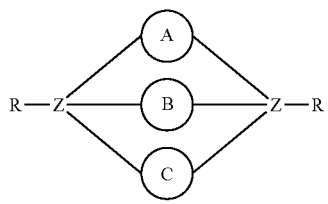

I in which Z is an atom with 3 or 4 valencies, R is nothing or represents hydrogen, a hydroxyl group, an amino group or a hydrocarbon radical, the divalent radicals Ⓐ, Ⓑ and Ⓒ are, independently of each other, hydrocarbon chains which optionally contain one or more hetero atoms and are optionally interrupted with a heteromacrocycle, at least one of the radicals Ⓐ, Ⓑ and Ⓒ also comprising at least one molecular unit or consisting essentially of a molecular unit having a triplet energy which is greater than that of the emission level of the complexed rare earth metal ion, characterized in that:

either at least one of the radicals Ⓐ, Ⓑ, and Ⓒ which does not comprise or does not consist essentially of said molecular unit comprises a pyridine radical substituted one or more times;

or at least one of the radicals Ⓐ, Ⓑ, and Ⓒ which does not comprise or does not consist essentially of said molecular unit comprises a pyridine radical which is substituted one or more times or unsubstituted and the radical(s) Ⓐ, Ⓑ or Ⓒ other than said radical is substituted with an electron-donating group.

The substituent(s) on the pyridine radical may be chosen, for example, from halogen, CN, $C_1$–$C_6$ carboxylic ester, OH, $NH_2$, $NO_2$, —$CH_2NHCONH$-aryl, —$CH_2NHCSNH$-aryl, —NHCONH—($C_1$–$C_6$)alkyl, —NHCSNH—($C_1$–$C_4$)alkyl, NHCONH-aryl, —NHCSNH-aryl, piperidyl, —N—($C_1$–$C_6$)alkylcarboxypiperidyl, ($C_1$–$C_4$)alkylamino-alkylamine, $C_1$–$C_{10}$ alkyl, alkenyl containing 2 to 10 carbon atoms, alkynyl containing 2 to 10 carbon atoms, cycloalkyl containing 3 to 8 carbon atoms, hydroxyalkyl containing 1 to 5 carbon atoms, alkoxy containing 1 to 10 carbon atoms, alkoxyalkyl containing 2 to 10 carbon atoms, alkoxyalkoxyalkyl containing 3 to 10 carbon atoms, alkoxyalkoxy containing 2 to 10 carbon atoms, alkenyloxy containing 2 to 10 carbon atoms, alkylthio containing 1 to 10 carbon atoms, alkylthioalkyl containing 2 to 10 carbon atoms, acylamino containing 1 to 7 carbon atoms, acylaminoalkyl containing 2 to 8 carbon atoms, carbamoylalkyl containing 2 to 5 carbon atoms, alkylaminocarbonylalkyl containing 3 to 9 carbon atoms, amino($C_1$–$C_6$)alkyl, amino($C_1$–$C_6$)alkylcarboxamide, amino($C_1$–$C_6$)alkylcarboxamido ($C_1$–$C_6$)alkyl and carboxy($C_1$–$C_{10}$)alkyl.

Preferably, a substituted pyridine will comprise one or 2 substituents. Substituents that are preferred for the purposes of the invention are, for example, the following substituents: amino($C_1$–$C_6$)alkyl, in particular aminomethyl or aminoethyl; amino($C_1$–$C_6$)alkylcarboxamide, in particular aminoethylcarboxamide, phenylcarbamoyl; phenylthiocarbamoyl; nitrile; piperidyl; $C_1$–$C_6$ carboxylic ester, in particular methylcarboxylate or ethylcarboxylate; amino($C_1$–$C_6$)alkylcarboxamido ($C_1$–$C_6$)alkyl, in particular aminocaproylamidomethyl and aminocaproylamidoethyl or carboxy ($C_1$–$C_{10}$)alkyl.

Preferably, the complexed rare earth metal ion is a europium ion.

Advantageously, the two radicals Ⓐ, Ⓑ or Ⓒ which do not comprise or do not consist essentially of a molecular unit having a triplet energy which is greater than that of the emission level of the complexed rare earth metal ion comprise a pyridine radical which is substituted one or more times or unsubstituted.

According to one preferred aspect, the molecular unit having a triplet energy which is greater than that of the emission level of the complexed rare earth metal ion is chosen from phenanthroline, anthracene, benzene, naphthalene, biphenyl, terphenyl, azobenzene, azopyridine, bipyridines and bisisoquinolines.

Advantageously, the molecular unit having a triplet energy which is greater than that of the emission level of the complexed rare earth metal ion is a bipyridine group.

Preferably, the bipyridine group(s) is (are) substituted with an electron-donating group chosen in particular from carboxylate, —$NH_2$, —NHAlk, —N(Alk)$_2$, OH, O⁻, —OAlk, Alk, —CH(Alk)$_2$, —C(Alk)$_3$, —NHCOAlk, and substituted or unsubstituted phenyl groups; Alk being a ($C_1$–$C_4$)alkyl group, the carboxylate group being particularly advantageous.

When the phenyl is substituted, it may be substituted with one or more substituents, which may be identical or different, chosen, for example, from sulfonate, carboxylate, methylcarboxylate, N,N-dimethylamino, methoxyethylcarboxylate and carboxamide.

The invention relates in particular to macropolycyclic complexes consisting of at least one rare earth metal salt complexed with a macropolycyclic compound corresponding to formula II:

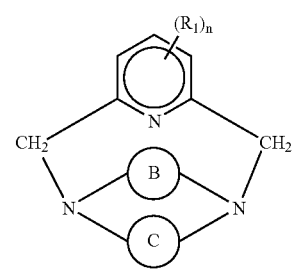

II in which:

the ring of formula

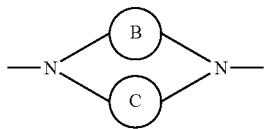

is the bis-bipyridine macrocycle of formula:

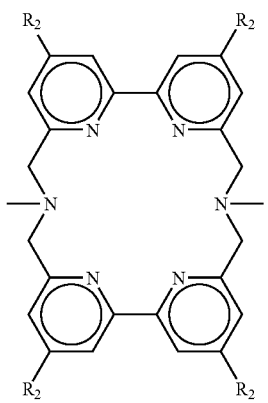

n=0, 1 or 2;

Y is a spacer group or spacer arm which consists of a divalent organic radical, chosen from linear or branched $C_1$ to $C_{20}$ alkylene groups optionally containing one or more double bonds and/or one or more heteroatoms such as oxygen, nitrogen, sulfur or phosphorus or one or more carbamoyl or carboxamido group(s); or else chosen from $C_5$ to $C_8$ cycloalkylene groups or from $C_6$ to $C_{14}$ arylene groups, said alkylene, cycloalkylene or arylene groups being optionally substituted with alkyl, aryl or sulfonate groups.

A is a functional group which can bond covalently with a biological substance;

$R_1$ is a group —COOR$_3$ in which $R_3$ is hydrogen or a $C_1$ to $C_{10}$ alkyl group and preferably represents a methyl, ethyl or tert-butyl group or $R_1$ is a group —CO—NH—Y-A or —Y-A;

$R_2$ is hydrogen, an electron-donating group, in particular carboxylate, —NH$_2$, —NHAlk, —N(Alk)$_2$, OH, O$^-$, —OAlk, Alk, —CH(Alk)$_2$, —C(Alk)$_3$, —NHCOAlk, substituted or unsubstituted phenyl; Alk being a ($C_1$-$C_4$)alkyl group or a group —CO—NH—Y-A or —Y-A, with the proviso that not more than one of the substituents $R_1$ and $R_2$ represents a group —CO—NH—Y-A or —Y-A and $R_1$ and $R_2$ do not simultaneously represent a group —CO—NH—Y-A or —Y-A, and with the proviso that when n=0, $R_2$ is other than hydrogen.

Preferred complexes are those in which the macropolycyclic compound corresponds to formula 11 in which:

n=0,

Y, A and $R_1$ are as defined above, and $R_2$ is as defined above and one of the substituents $R_2$ is a group —CO—NH—Y-A or —Y-A.

Complexes that are particularly advantageous are the europium cryptates [Eu$^{3+}$⊂Py.Bpy(CO$_2$H)$_2$.Bpy(CO$_2$H)$_2$], [Eu$^{3+}$⊂bpy(CO$_2$H)$_2$.bpy(CO$_2$H)$_2$.Py(NH$_2$)$_2$] and [Eu$^{3+}$⊂bpy(CO$_2$H)$_2$.bpy(CO$_2$H)$_2$. Py(CONH(CH$_2$)$_2$NHR$_4$]$_2$ in which

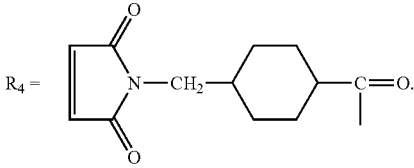

The rare earth metal macropolycyclic complexes according to the invention are prepared by the processes mentioned above.

The invention also relates to fluorescent conjugates consisting of the rare earth metal macropolycyclic complexes as defined above, bonded covalently to one of the members of a pair of molecules capable of bonding together specifically, in particular a polypeptide, a protein, a cell receptor, an antigen, an antibody or a nucleic acid.

According to a further aspect, the invention also relates to the use of a rare earth metal macropolycyclic complex as defined above, for reducing the fluorescence quenching caused by the measuring medium, in a fluorescence assay of an analyte.

The invention is illustrated by the examples below, in which the techniques used to characterize and identify the compounds are as follows:

The melting points were determined using a capillary melting point apparatus: electrothermal IA8103; they are uncorrected.

The thin layer chromatographies (TLC) were carried out on Macherey-Nagel plates: Al$_2$O$_3$ (Polygram Alox N/UV254) and SiO$_2$ (Polygram SIL 6/UV254) containing a fluorescent indicator.

The liquid chromatographies (HPLC) were carried out using an LKB chromatographic system composed of the following components: 2152 microprocessor, 2150 pump, Uvicord 2158 detector; Merck 50734 Lichrosphes 100RP18 column; gradient applied [time (min)-flow rate/ml) proportion of the solvent B (%): 0-1-15; 5-1-15; 35-1-1001; solvent A=H$_2$O containing 1% TFA, solvent B=CH$_3$CN.

The retention times Tr are expressed in minutes.

The NMR spectra were recorded using a Bruker AC 250 machine [250 ($^1$H); 62.9 ($^{13}$C)]. The chemical shifts are given in ppm relative to the corresponding internal reference.

For the measurements regarding ($^1$H): CHCl$_3$=7.26; CH$_3$OH=3.34; tBuOH=1.36. The following symbols were used:

s=singlet d=doublet t=triplet m=multiplet

AB=coupling system

J=coupling constant

For the measurements regarding carbon ($^{13}$C): CHCl=77.0, the following symbols were used: Ct=tertiary carbon; Cq=quaternary carbon.

The ionization methods used for the mass spectra are FAB$^+$=fast atom bombardment in positive mode (MNBA matrix: meta-nitrobenzyl alcohol or thioglycerol) and electron impact EI.

The absorption spectra (UV-visible) were recorded using a Perkin Elmer lambdal 5 spectrophotometer with $10^{-5}$ M solutions.

The invention is illustrated by the examples below in which the following abbreviations are used:
AIBN: azobisisobutyronitrile
HPLC: high performance liquid chromatography
M.A.: microanalysis
m.p.: melting point
M.S.: mass spectrum
NBS: N-bromosuccinimide
$^1$H NMR: proton nuclear magnetic resonance
$^{13}$C NMR: carbon-13 nuclear magnetic resonance
SPDP: N-succinimidyl 3-(2-pyridylthio)propionate
Sulfo-SMCC=3-sulfo-N-hydroxysuccinimide ester of 4-(N-maleimidomethyl)cyclohexane-1-carboxylic acid
TFA: trifluoroacetic acid
TLC: thin layer chromatography
TMS: tetramethylsilane

EXAMPLE 1

Preparation of the macrobicycle of formula (6) bpy.bpy.py(CO$_2$Me)

Alkylation of the macrocyclic diamine (5) with the dibromomethyl derivative (4) gives the compound (6) represented below.

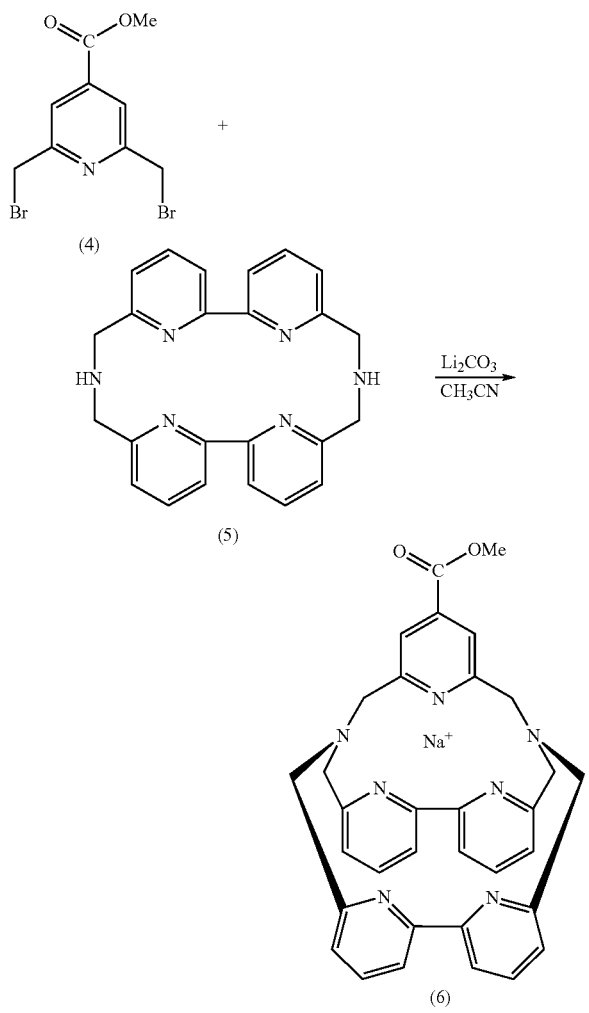

a) Preparation of 4-methyl 2,6-dibromomethylisonicotinate (4)

The sequence of reactions represented below allows compound (4) to be isolated.

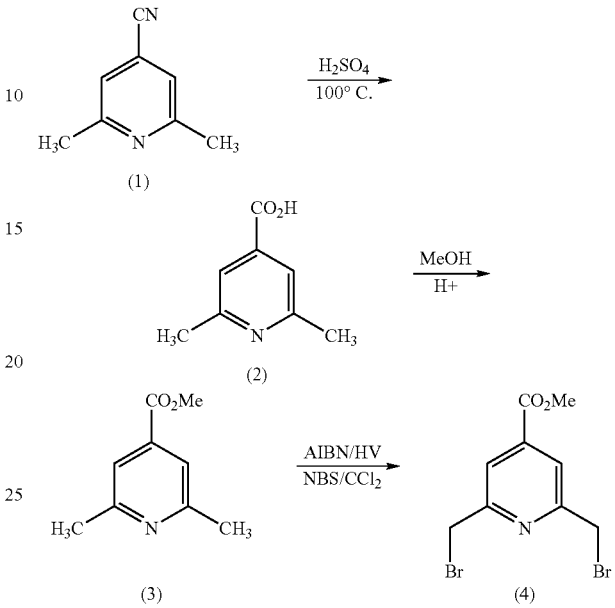

4-Cyano-2,6-dimethylpyridine (1)

The studies by W. E. Feely and E. M. Beavers described in J. Am. Chem. Soc., 1959, 81, 4004 regarding the cyanation of amine oxide salts make it possible to obtain compound (1).

2,6-Dimethylisonicotinic acid (2)

A mixture of 1 g (7.56 mmol) of (1) and 5 ml of concentrated sulfuric acid is heated at 100° C. for 5 hours. The resulting solution is then cooled on an ice bath, brought to pH 3.5 with 10 N sodium hydroxide and then concentrated to dryness. Extraction with ether for 48 hours (soxhlet) of a portion of the residue obtained gives 50 mg of 2,6-dimethylisonicotinic acid (2) for analysis. The remaining crude reaction product, not treated with ether, is used in its present form in the esterification reaction without further purification.

NMR: $^1$H (D$_2$O); internal reference tBuOH 1.29 ppm. 2.82 (s, 6H, CH$_3$); 8.05 (s, 2H, Py).

MS (EI): 151 (M+, 100); 134 (M+—OH, 7.2); 106 (M+—CO$_2$H, 16.4)

MA: C$_8$H$_9$NO$_2$+0.1 NaHSO$_4$ (163.16)
calculated: C 58.89 H 5.62 N 8.58 O 23.53
found: C 58.73 H 5.90 N 8.37 O 23.7

-4-Methyl 2,6-dimethylisonicotinate (3)

A mixture of 2 g of 2,6-dimethylisonicotinic acid (2) (unpurified), 100 ml of methanol and 1 ml of 98% sulfuric acid is refluxed for 24 hours. After cooling, the reaction medium is neutralized with saturated NaHCO$_3$ solution and then extracted five times with 60 ml of CHCl$_3$. The combined chloroform phases are then dried over Na$_2$SO$_4$ and then concentrated. The resulting solid is then extracted four times with 50 ml of ether, after which the ether phase is concentrated. Chromatography on alumina [gradient: cyclohexane/CH$_2$Cl$_2$ (50/50) to pure CH$_2$Cl$_2$] of the white residue obtained gives 1 g of 4-methyl-2,6-dimethyl isonicotinate (3).

m.p.: 45–47° C.

TLC: Rf: 0.3 [SiO$_2$/CH$_2$Cl$_2$—MeOH (97/3)]

HPLC: Tr: 2.4

UV: CHCl$_3$: 290.6 nm (3650)

NMR: $^1$H CDCl$_3$; internal reference TMS 2.59 (s, 6H, CH$_3$); 3.93 (s, 3H, CO$_2$CH$_3$); 7.51 (s, 2H, Py)

$^{13}$C CDCl$_3$; internal reference 77.0 ppm 24.5 (CH$_3$); 52.5 (OCH3); 119.5 (Ct); 137.9, 158.9 (Cq); 166.1 (C=O).

MS (EI): 165 (M+, 24); 134 (M+—OCH$_3$, 13); 106 (M+—CO$_2$Me)

4-Methyl-2,6-dibromomethyl Isonicotinate (4)

A mixture of 1.372 g (8.3 mmol) of (3), 60 mg of AIBN and 2.866 g (16.1 mmol) of NBS in 120 ml of CCl$_4$ is refluxed under a nitrogen atmosphere and under irradiation with a 100 W lamp, for 8 hours. The reaction medium is then returned to room temperature, after which it is washed with 200 ml of saturated NaHCO$_3$ solution. After removing the lower phase (CCl$_4$), the aqueous phase is extracted 4 times with 50 ml of CHCl$_3$; the combined organic extracts are then washed with 100 ml of H$_2$O, dried (Na$_2$SO$_4$) and then concentrated to dryness. Purification of the residue obtained by chromatography on silica [gradient: cyclohexane-CH$_2$Cl$_2$ (80/20) to pure CH$_2$Cl$_2$) makes it possible to separate out a first fraction of the bromo derivative (4), from the polybromo species, from a mixture of isomers of symmetrical and asymmetrical dibromo derivatives and from the monobromo species also formed.

In order to have available a larger amount of methyl 2,6-dibromomethyl isonicotinate, the monobromo compound isolated above [0.543 g (2.2 mmol)] is mixed with 0.4 g (2.2 mmol) of NBS, 23 mg of AIBN and 50 ml of CCl$_4$ and is then treated under the above bromination conditions to give a second fraction of (4).

Finally, a purification by chromatography on silica [gradient: pure cyclohexane to cyclohexane/EtOAc (85/15)] of the mixtures of dibromoisomers, isolated in the above two reactions, gives a final fraction of (4), i.e. 596 mg in total (22%).

m.p.: 90–92° C.

TLC: Rf: 0.6 (SiO$_2$/CH$_2$Cl$_2$)

HPLC: Tr: 20 min 5 sec

UV: CHCl$_3$: 290.8 nm (4270); 240.3 nm (3010)

NMR: $^1$H CDCl$_3$; internal reference TMS 3.98 (s, 3H, CH$_3$); 4.58 (s, 4H, CH$_2$); 7.92 (s, 2H, Py)

$^{13}$C CDCl$_3$; internal reference 77.0 ppm 32.8 (CH$_2$); 52.9 (OCH$_3$); 122.2 (Ct); 139.8, 157.9 (Cq); 164.7 (C=O).

MS (EI): 322.9 (M+, 15); 243.9 (M+—Br, 100); 163 (M$^+$—2Br, 15.7).

MA: C$_9$H$_9$NO$_2$Br$_2$ (322.98)

Calculated: C 33.47H 2.80 N 4.33 O 9.90

Found: C 33.69H 2.81 N 4.29 O 10.17 b) Preparation of the alkali metal cryptate (Na$^+$⊂ bpy.bpy.pyCO$_2$Me] Br$^-$ of formula (6).

A mixture of 0.2 g (0.508 mmol) of bipyridine macrocyclic diamine (5) (described in J. Org. Chem., 1983, 48, 4848) and 0.376 g (5.08 mmol) of Li$_2$CO$_3$ in 400 ml of CH$_3$CN is refluxed for 40 min under a nitrogen atmosphere. A solution of 0.165 g (0.508 mmol) of 4-methyl 2,6-dibromomethyl-isonicotinate (4) in 100 ml of CH$_3$CN is added dropwise (2 hours) to the resulting suspension. At the end of the addition, stirring is continued under the same conditions for a further 22 hours and the reaction medium is then cooled on an ice bath. The carbonate is then filtered off and the filtrate is evaporated to dryness. A chromatography on silica [gradient: CH$_2$Cl$_2$ containing 10% MeOH] of the residue obtained gives 117.5 mg of compound (6) (35%).

TLC: Rf: 0.4 [Al$_2$O$_3$/CHCl$_3$—MeOH (90/10)]

HPLC: Tr: 4 min 1 sec

UV: CHCl$_3$: 246 nm (27950); 291 nm (27410).

NMR: $^1$H (CDCl$_3$); internal reference TMS.

3.94 (s, 3H, CH$_3$); 4.00 (d, J=15 Hz, AB, 4H, CH$_2$);

4.08 (d, J=14.7 Hz, AB, 4H, CH$_2$); 4.09 (s, 4H, CH$_2$);

7.39–7.42 (m, 4H, BPy); 7.77 (s, 2H, Py); 7.85–7.89 (m, 8H, BPy).

$^{13}$C (CDCl$_3$); internal reference 77 ppm.

52.9 (CH$_3$, CO$_2$Me); 59.4 (CH$_2$); 59.5 (CH$_2$);

C$_t$ (119.9; 122.1; 123.4; 138.8)

C$_q$ (139.2; 154.6; 158.5; 159.6); 165.3 (CO$_2$Me).

MS(FAB$^+$): Thioglycerol matrix.

578.2 (Ligand-Li$^+$+Na$^+$, 100%); 556.2 (Ligand-Li$^+$+H, 10%).

Thioglycerol matrix+1% TFA 578 (Ligand-Li$^+$+Na$^+$, 20%); 556.1 (Ligand-Li$^+$+H, 100%).

MA: C$_{33}$H$_{29}$N$_7$O$_2$NaBr, 3H$_2$O (712.53).

Calculated: C 55.62H 4.95 N 13.76

Found: C 55.93H 4.73 N 13.61

EXAMPLE 2

Preparation of the europium cryptate [Eu$^{3+}$ ⊂bpy.bpy.pyCO$_2$Me]Cl$^-$$_3$ of Ligand (6) of Example (1)

11.8 mg of EuCl$_3$, 6H$_2$O (3.22×10$^{-5}$ mol) are added to 20.2 mg (2.84×10$^{-5}$ mol) of the macrobicycle (6) contained in 5 ml of anhydrous methanol. The resulting homogeneous mixture is refluxed under a nitrogen atmosphere for 23 hours. Next, addition to this solution, cooled to room temperature, of 4 ml of ether causes the crystallization of 14.2 mg (52%) of the europium cryptate.

HPLC: Tr: 14.1

UV: H$_2$O: 250 nm (18270); 309 nm (24400).

MS(FAB$^+$): Nitrobenzyl alcohol matrix

778 [(Eu$^{3+}$⊂L+2Cl$^-$)$^+$, 40%]; 743 [(Eu$^{2+}$⊂L+Cl$^-$)$^+$, 90%];

707 [(Eu$^{3+}$⊂L-2H)$^+$, 100%]

MA: C$_{33}$H$_{29}$N$_7$O$_2$EuCl$_3$, 0.13 EuCl$_3$, NaBr, 2 CH$_3$OH (1014.51)

Calculated: C 41.43H 3.67 N 9.66

Found: C 41.23H 3.95 N 9.63

EXAMPLE 3

Preparation of the macrobicycle of formula (12) Py.Bpy(CO$_2$Et)$_2$.BPY(CO$_2$Et)$_2$ This compound is prepared according to the scheme represented below.

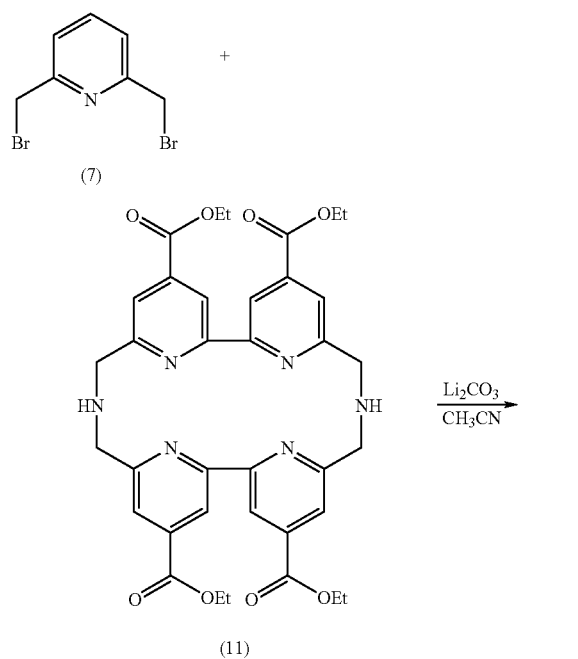
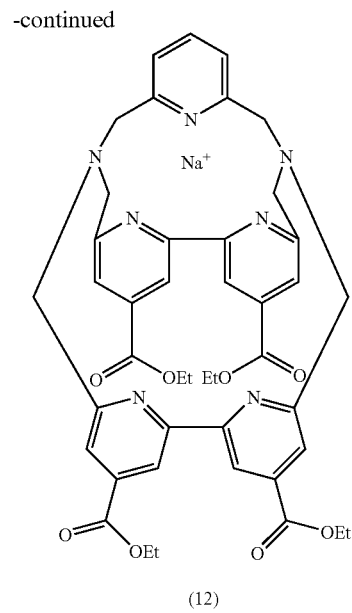
a) Preparation of the macrocycle of formula (11)
The following reaction sequence gives the bpy.bpy diamine tetraester macrocycle (11).
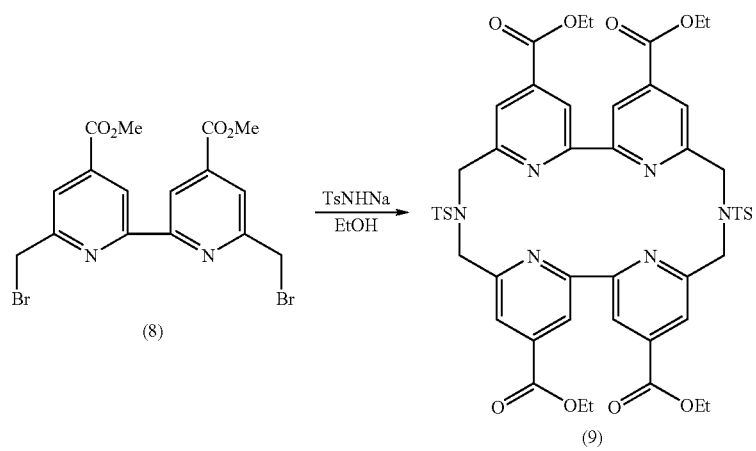
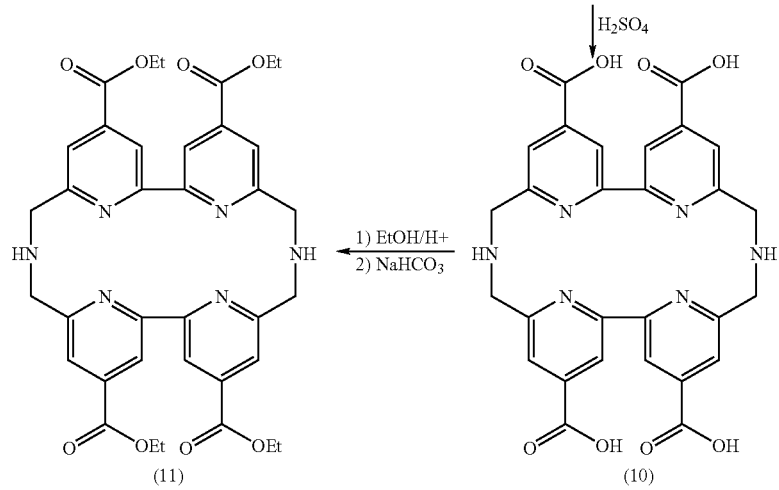
-Tosyl bpy.bpy tetraester macrocycle (9)

A mixture of 5.5 g (12 mmol) of 6,6'-dimethyl 2,2'-dibromomethyl-4,4'-bipyridinedicarboxylate (8) (described in Helv. Chim. Acta, 1988,71,1042), 4.64 g of freshly prepared sodium salt of tosylamide (24 mmol) and 900 ml of absolute ethanol is refluxed under a nitrogen atmosphere for 26 hours. This suspension is then cooled for 1 hour on an ice bath, after which it is filtered. The isolated precipitate is then washed with 700 ml of water, 500 ml of ethanol and 20 ml of chloroform to give 1.88 g (31.6%) of (9).

TLC: Rf: 0.7 (SiO$_2$/CHCl$_3$—MeOH (99/1)]
HPLC: Tr: 36.1
MS (FAB)$^+$: MNBA matrix
991 (M+, 45%); 835 (L-Tos, 12%).
MA: C$_{50}$H$_{50}$O$_{12}$N$_6$S$_2$ NaBr. (1094)
Calculated: C 54.89H 4.6 N 7.68 S 5.86 Na 2.1
Found: C 55.66H 4.64 N 7.75 S 6.04 Na 3.19

Bpy.Bpy. tetraacid macrocycle (10)

A solution of 0.15 g (0.15 mmol) of the tosyl macrocycle (9) in 1 ml of concentrated H$_2$SO$_4$ is heated at 100° C. for 3 hours under a nitrogen atmosphere. The reaction medium is then cooled on an ice bath, diluted by addition of 5 ml of water and then brought to pH 3.0 by adding 7 ml of 5N NaOH. The precipitate formed is then filtered off, washed thoroughly with water (50 ml) and then dried. The tetraacid macrocycle (10) thus isolated (probably in the form of the amine salt) is used without further purification in the next step.

Bpy.Bpy.diamine tetraethylester macrocycle (11)

A suspension of 53 mg of compound (10) in 100 ml of absolute ethanol and 0.5 ml of concentrated H$_2$SO$_4$ is refluxed under a nitrogen atmosphere for 28 hours. The resulting homogeneous solution is then successively cooled on an ice bath, neutralized with saturated NaHCO$_3$ solution and treated with 80 ml of CHCl$_3$ (4×20) to give 60 mg of compound (11) (quantitative).

TLC: Rf: 0.7 [Al$_2$O$_3$/CH$_2$Cl$_2$—MeOH (80/20)]
HPLC: Tr: 17.2
UV: CHCl$_3$: 243.1 nm (24150); 303.2 nm (25210).
NMR: $^1$H (CDCl$_3$); internal reference TMS.
1.44 (t, J=7.0 Hz, 12H, CH$_3$); 2.29 (s, broad, NH); 4.17 (s, 8H, CH$_2$)
4.39 (q, J=6.9 Hz, 8H, CH$_2$ ester); 7.43 (d, J=1.4 Hz, 4H, BPy);
8.29 (d, J=1.1 Hz, 4H, BPy).
$^{13}$C (CDCl$_3$); internal reference 77.0 ppm.
14.9 (CH$_3$, CO$_2$CH$_2$CH$_3$); 56.8 (CH$_2$); 62.3 (CO$_2$CH$_2$CH$_3$);
Ct (119; 122.5); Cq (138.9; 158.9; 161.4); 165.7 (CO$_2$C$_2$H$_5$)
MS(FAB$^+$): Thioglycerol matrix
683 (M$^+$, 100)
MA: C$_{36}$H$_{38}$N$_6$O$_8$, H$_2$O (700.74)
Calculated: C 61.7H 5.75 N 11.99
Found: C 62.2H 6.01 N 11.48 b) Preparation of the alkali metal cryptate of formula (12) [Na$^+$ ⊂ Py.Bpy(CO$_2$Et)$_2$.Bpy(CO$_2$Et)$_2$]Br$^-$ A mixture of 180.7 mg (0.265 mmol) of macrocyclic diamine (11) and 195.5 mg (2.65 mmol) of Li$_2$CO$_3$ in 360 ml of anhydrous CH$_3$CN is refluxed for 35 min under a nitrogen atmosphere. A solution of 70.7 mg (0.267 mmol) of 2,6-dibromomethylpyridine (7) [the preparation of this compound has been described by Vogtle, starting with lutidine: Synthesis, 1977, 273] in 360 ml of anhydrous CH$_3$CN is added slowly (5 hours) to the resulting suspension. Reflux is maintained for 72 hours and the reaction medium is then cooled on an ice bath. After filtration of the insoluble carbonates, the filtrate is evaporated to dryness. The residual solid obtained is chromatographed on a column of alumina with CH$_2$Cl$_2$/EtOH as eluent (99/1 to 85/15) to give 78 mg of (12) (33%).

TLC: Rf=0.6 [Al$_2$O$_3$/CHCl$_3$—MeOH (90/10)]
HPLC: Tr=20.8
UV: CHCl$_3$: 250 nm (24900); 316 nm (18900)
NMR: $^1$H (CDCl$_3$); internal reference TMS
1.45(t, J=7.1 Hz, 12H, CH$_3$); 4.07 (s, 4H, CH$_2$); 4.14 (d, J=15.4 Hz, AB, 4H, CH$_2$); 4.22 (d, J=15.3 Hz, AB, 4H, CH$_2$); 4.46 (q, J=7 Hz, 8H, CH$_2$ ester); 7.27(d, J=7.7 Hz, 2H,Py); 7.66 (t, j=7.7 Hz, 1H, Py); 7.93(s, 4H, Bpy);
8.42(s, 4H, Bpy).
$^{13}$C (CDCl$_3$); internal reference 77 ppm.
14.3 (CH$_3$, CO$_2$Et); 59.4 (CH$_2$); 59.5 (CH$_2$); 62.5 (CH$_2$, CO$_2$Et); Ct (119.3; 122.8; 123; 138.1); Cq (140.5; 155.1; 157.8; 160.1); 164.5 (CO$_2$Et).
MS: (FAB$^+$/NBA matrix)
808.4 (ligand-Li$^+$+Na$^+$, 100%); 663.3 (ligand+Na$^+$-2CO$_2$Et, 5%).
MA: C$_{43}$H$_{43}$N$_7$O$_8$NaBr, CH$_2$Cl$_2$ (972.68)
Calculated: C 54.3H 4.6 N 10
Found: C 54.9H 4.0 N 9.8

EXAMPLE 4

Preparation of the Europium Cryptate of Formula 12a [Eu$^{3+}$ ⊂ Py.Bpy(CO$_2$H)$_2$.BPY(CO$_2$H)$_2$]

(12a)

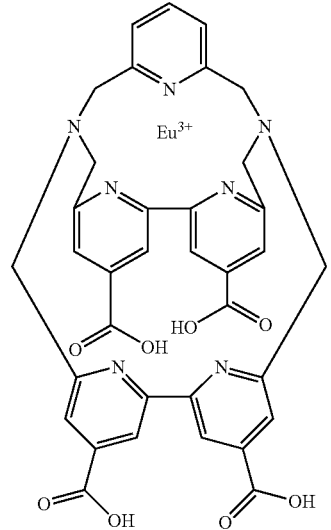

a) Preparation of the europium complex of ligand 12 of Example 3 [Eu$^{3+}$ ⊂ Py.Bpy(CO$_2$Et)$_2$ Bpy(CO$_2$Et)$_2$]

33 mg (9×10$^{-5}$ mol) of EuCl$_3$0.6H$_2$O are added to 69 mg (7.7×10$^{-5}$ mol) of the sodium cryptate (12) contained in 32 ml of anhydrous CH$_3$CN. The resulting suspension is refluxed under a nitrogen atmosphere for 27 hours; after cooling, the solvent is evaporated off. Next, a reverse-phase chromatography of the residue obtained gives 25 mg of the europium cryptate [Eu$^{3+}$ ⊂ 12] (25%).

HPLC: Tr: 21
UV: EtOH/330 nnm (21000)
MS: (FAB$^+$) thioglycerol matrix
1164.2 [(Eu$^{3+}$ ⊂ 12+2CF$_3$CO$_2$$^-$)$^+$,64%
1051.8 [Eu$^{3+}$ ⊂ 12+CF$_3$CO$_2$$^-$+H) 100%]
937.4 [(Eu$^{2+}$ ⊂ 12-1H) 35%]

19 b) Preparation of the acid cryptate of formula 12a

100 µl of aqueous 1.6 M sodium hydroxide solution are added to an aqueous solution of 10 mg (7.83×10⁻⁶ mol) of europium cryptate (Eu³⁺⊂12]. The resulting mixture is stirred for 2 hours at room temperature and is then evaporated to dryness. Purification by (reverse-phase) chromatography with a mixture of $H_2O$ containing 1% $TFA/CH_3CN$ as eluent, of the residue obtained, gives 8 mg (quantitative) of the europium cryptate of formula 12a.

EXAMPLE 5

Preparation of the pyridine diethyl ester bispyridine tetra-tert-butyl ester macrobicycle of formula (16)

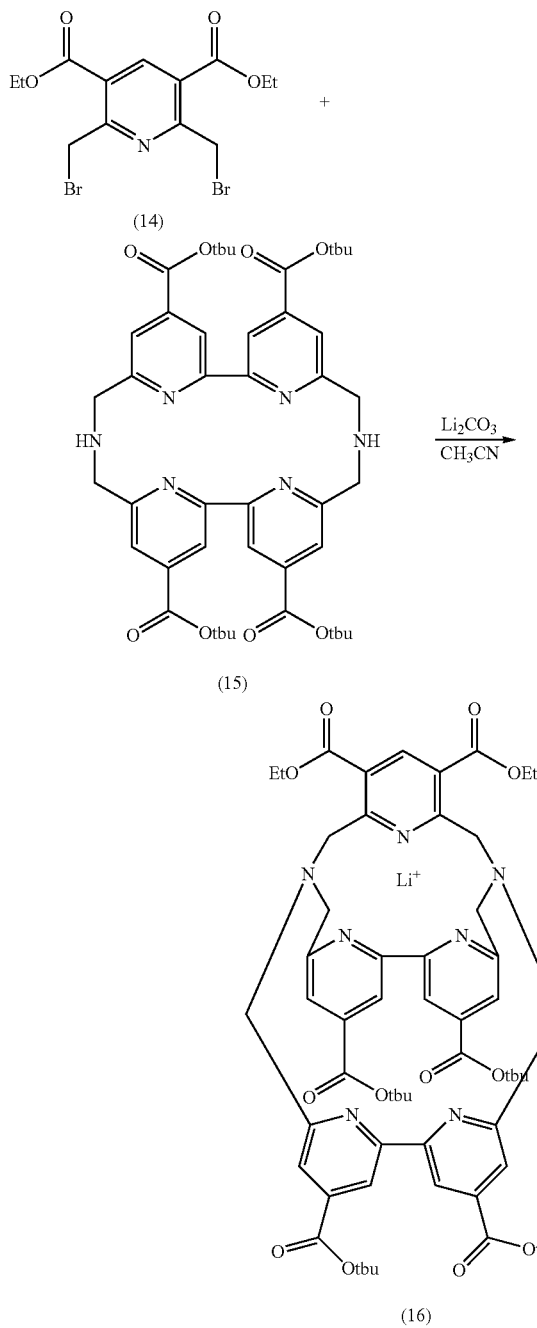

20 a) Preparation of diethyl 2,6-dibromomethyl-3,5-pyridinecarboxylate of formula (14)

This compound is synthesized according to a conventional free-radical bromination procedure starting with commercial diethyl 2,6-dimethyl-3,5-pyridinecarboxylate.

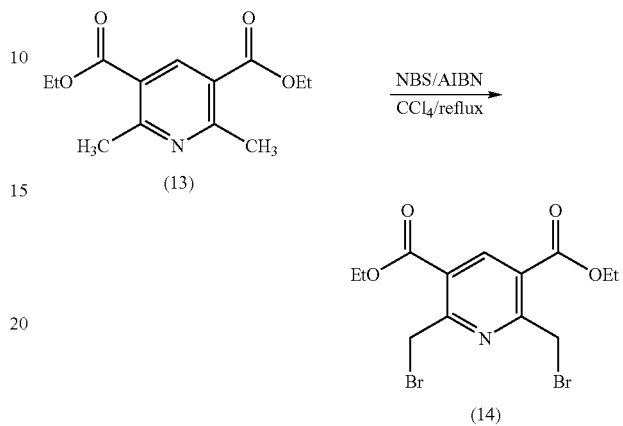

A mixture of 0.5 g (2 mmol) of 2,6-diethyl 3,5-dimethylpyridinecarboxylate, 0.89 g (5 mmol) of NBS and 4 mg of AIBN in 20 ml of carbon tetrachloride is refluxed for two hours under irradiation with a 100 W visible lamp. Next, the suspension is cooled on an ice bath and then filtered in order to remove the succinimide formed. The filtrate is then concentrated to dryness; chromatography on silica of the residue obtained, with a hexane/chloroform mixture as eluent (gradient: 50/50 to 30/70) gives 195 mg of bromo derivative of formula (14) (26%).

TLC: Rf=0.4 ($SiO_2/CH_2Cl_2$)

HPLC: Tr=25.5

UV: $CHCl_3$/245 nm (9400)

NMR: $^1H$ ($CDCl_3$); internal reference TMS 1.45 (t, J=7.0 Hz, 6H, $CH_3$); 4.47 (q, J=7.2 Hz, 4H $CH_2$); 5 (s, 4H, $CH_2Br$); 8.80 (s,1H, Py).

b) Preparation of the diamine bisbipyridine tetra-tert-butyl ester macrocycle of formula (15).

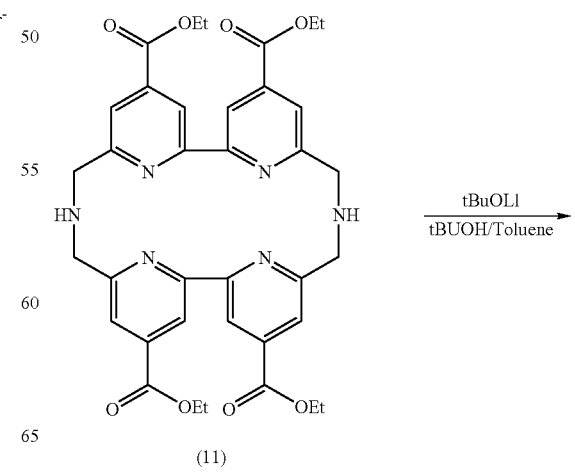

-continued

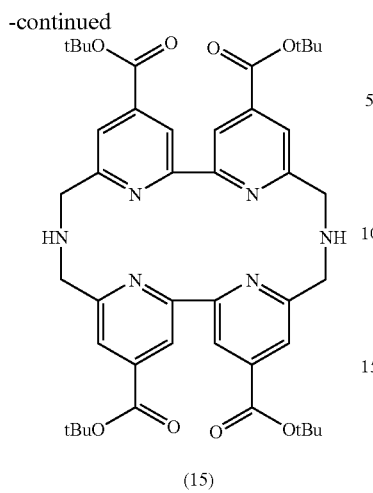

(15)

This compound is synthesized by simple transesterification starting with lithium tert-butoxide and the macrocycle (11) of Example 3.

A mixture of 251 mg of macrocycle (11) (0.36 mmol), 363 mg (4.5 mmol) of lithium tert-butoxide, 35 ml of dry toluene and 35 ml of dry tert-butanol is heated at 80° C. under a stream of nitrogen for about 3 hours. After cooling, the tert-butanol is removed by evaporation; the residual organic phase is first washed with water to neutral pH (6×50 ml) and then successively dried over $Na_2SO_4$, filtered and concentrated to dryness. Reverse-phase chromatography of the residue obtained with $CH_3CN$ and $H_2O$ containing 1% TFA as eluents gives 117 mg of the macrocycle (15) (40%).

HPLC: Tr=22.4

UV: $CHCl_3$/311 nm (18000); 280 nm (8300); 268 nm (7200)

NMR: $^1H$ ($CDCl_3$); internal reference TMS 1.65 (s, 36H, $CH_3$); 4.69 (s, 8H, $CH_2$); 7.97 (s, 4H, H bpy); 8.51 (s, 4H, Hbpy).

MS: (ES) 796 (M+H).

c) Preparation of the alkali metal cryptate of formula (16) $[Li^+ \subset bpy(CO_2tbu)_2.bpy(CO_2tbu)_2.Py(CO_2Et)_2]Br^-$ A mixture of 25.3 mg ($3.18 \times 10^{-5}$ mol) of macrocycle (15) and 27 mg ($3.65 \times 10^{-4}$ mol) of $Li_2CO_3$ in 25 ml of anhydrous $CH_3CN$ is refluxed for 15 min under a stream of nitrogen. A solution of 12.7 mg ($3.1 \times 10^{-5}$ mol) of 2,6-diethyl 3,5-dibromomethylpyridinecarboxylate (14) in 12 ml of anhydrous $CH_3CN$ is added dropwise over 10 min to the resulting suspension. Stirring is continued under these conditions for 23 hours and the reaction medium is then cooled on an ice bath, after which it is filtered. After evaporating the filtrate to dryness, reverse-phase chromatography of the residue obtained gives 12 mg (35%) of macrobicycle (16).

HPLC: Tr=28.5

MS: (ES) 1042.3 [ligand-$Li^+$—$Br^-$(100%)]; 1064.3 [ligand-$Li^+$—Br+$Na^+$(30%)]

EXAMPLE 6

Preparation of the europium cryptate of formula (19) $[Eu^{3+} \subset bpy(CO_2H)_2.bpy(CO_2H)_2.Py(NH_2)_2]$

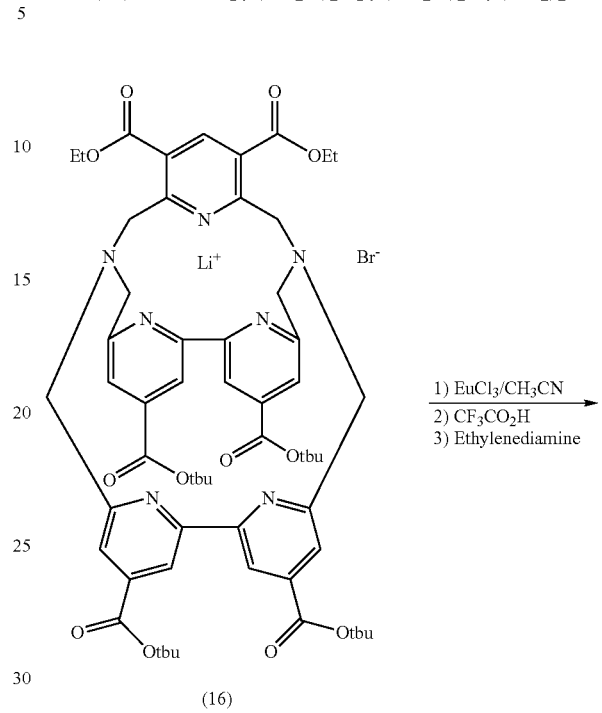

(16)

1) $EuCl_3$/$CH_3CN$
2) $CF_3CO_2H$
3) Ethylenediamine

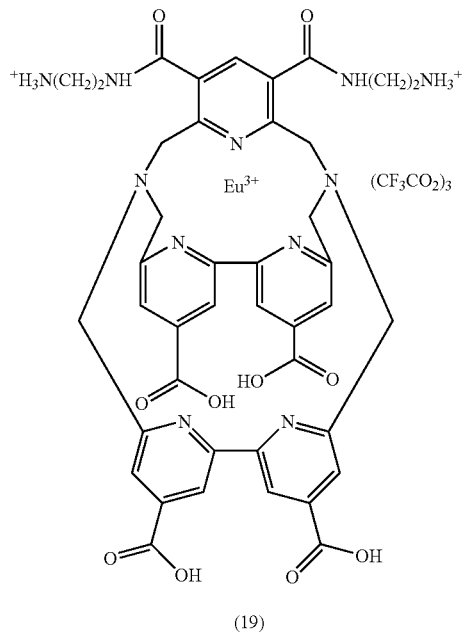

(19)

a) Preparation of the europium complex of the ligand (16) of Example (6) $[Eu^{3+} \subset bpy(CO_2tbu)_2.bpy.(CO_2tbu)_2.Py(CO_2Et)_2$ 12.8 mg ($3.5 \times 10^{-5}$ mol) of $EuCl_3.6H_2O$ are added to a solution of 17.1 mg ($1.51 \times 10^{-5}$ mol) of lithium cryptate (16) in 10 ml of anhydrous acetonitrile. The reaction mixture is then refluxed under a stream of nitrogen for 3 hours. After cooling, the solvent is evaporated off and the residue obtained (m=27.6 mg) is used without further purification in the following step.

b) Preparation of the acid europium cryptate [Eu$^{3+}$⊂bpy(CO$_2$H)$_2$.bpy(CO$_2$H)$_2$.Py(CO$_2$Et)$_2$](CF$_3$CO$_2^-$)$_3$ This reaction consists in selectively hydrolyzing the tert-butyl esters borne by the bipyridine subunits by treatment with pure trifluoroacetic acid.

27.6 mg of the residue obtained in paragraph a) of Example 6 are dissolved in 14 ml of trifluoroacetic acid. The resulting homogeneous solution is stirred for 4 hours at room temperature and then concentrated to dryness by evaporating the acid under vacuum. Reverse-phase chromatography with a mixture of H$_2$O containing 1% TFA/CH$_3$CN as eluents gives 10.4 mg of the europium cryptate [Eu$^{3+}$⊂bpy(CO$_2$H)$_2$.bpy(CO$_2$H)$_2$.Py(CO$_2$Et)$_2$](CF$_3$CO$_2^-$)$_3$ HPLC: Tr=13.7

UV: MeOH/324.6 nm (16000); 337 nm (13300)

c) Preparation of the europium cryptate of formula (19)

A solution of 300 μl of ethylenediamine (4.45×10$^{-3}$ mol) in 300 μl of anhydrous MeOH is added over 5 min, while cooling on an ice bath and under a stream of nitrogen, to a solution of 10 mg (8.03×10$^{-6}$ mol) of europium cryptate [Eu$^{3+}$⊂bpy(CO$_2$H)$_2$.bpy(CO$_2$H)$_2$.Py(CO$_2$Et)$_2$] in 2 ml of anhydrous MeOH. The temperature of the medium is then raised gradually to 20° C., followed by stirring for 2.5 hours under these conditions. After evaporating off the solvent, reverse-phase chromatography of the resulting residue with a mixture of H$_2$O containing 1% TFA/CH$_3$CN as eluents gives 5.5 mg of cryptate (19) (45%).

UV: MeOH/325 nm (17000)

EXAMPLE 7

Preparation of the europium cryptate of formula (20)

This compound is prepared according to the scheme represented below.

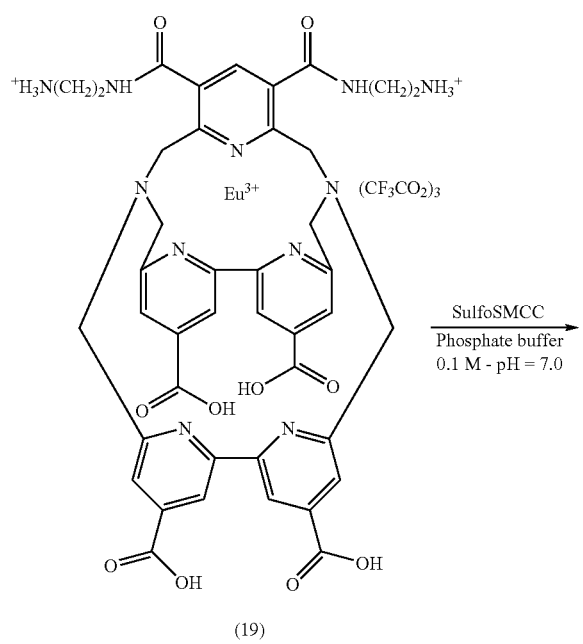

(19)

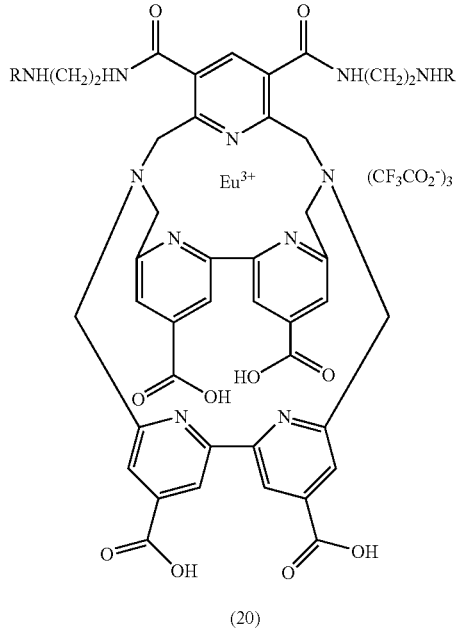

(20)

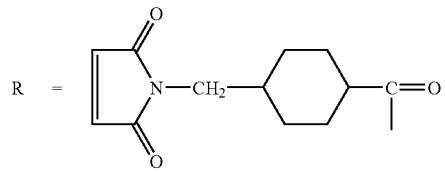

A solution of 195 μg (4.45×10$^{-7}$ mol) of sulfoSMCC in 168 μl of phosphate buffer is added dropwise over 45 min to a solution, cooled on an ice bath, of 0.2 mg (1.28×10$^{-7}$ mol) of compound (19) in 200 μl of 0.1 M pH 7.0 phosphate buffer. At the end of the addition, the temperature of the medium is returned to 20–25° C. and the reaction is continued under these conditions for 3 hours. Next, direct purification by reverse-phase chromatography with a mixture of H$_2$O containing 1% TFA/CH$_3$CN as eluent gives 100 μg of cryptate (20) (50%).

EXAMPLE 8

Coupling of the compound of formula (20) with protein a) Activation of the protein 3.14 mg (4.43 mg/ml) of antibody (free PSA, cloneA455, CIS bio international, France) are activated for 30 min at room temperature, in 0.1 M pH 7.0 phosphate buffer, by adding 26.2 μl of an ethanolic solution of SPDP at 2 mg/ml (initial reagent/protein molar ratio: 8). At the end of this period, thiol functions (SH) are generated by adding to the reaction medium 37 μl of a dithiothreitol (DTT) solution at 61.7 mg/ml in 0.1 M pH 7.0 phosphate buffer and incubating for 15 min at room temperature; next, the mixture is purified on a Sephadex G25 HR10-10 column with the buffer used during the activation as eluent.

b) Coupling of the activated protein and the cryptate of formula (20)

55 μl of a solution containing 1 mg/ml in 0.1M pH 7.0 phosphate buffer of cryptate of formula (20) are added to 386 μl of a solution of antibody A455 (1.2 mg/ml in the same buffer) activated according to the procedure described in paragraph a) of Example 8, followed by incubation for 20 hours at 4° C.; at the end of this period, the reaction mixture is purified on a Sephadex G25 HR10-30 column with the buffer for the coupling reaction as eluent. Absorbance measurements of the antibody-cryptate conjugate at 280 nm and 325 nm give a degree of labeling of 8.0 and a yield of 80%.

EXAMPLE 9

Demonstration of the low sensitivity to quenching of the pyridine cryptates of Examples 2, 4(b), 6(c), 7 and 8 in serum The determinations below were carried out with a Perkin-Elmer LS50 spectrofluorimeter.

The fluorescence lifetime measurements for the cryptates tested were carried out according to the procedure disclosed in EP 0 601 113.

The compounds were tested in a 0.1 M pH 7.0 phosphate buffer and in newborn calf serum (NCS). The solutions for measuring cryptate concentration of about $10^{-6}$ M/l were prepared by diluting the stock solution to 1/100 either with the buffer alone or with a mixture of 2/3 buffer to 1/3 serum.

The pyridine cryptates of Examples 2, 4(b), 6(c), 7 and 8 were tested in comparison with the trisbipyridinediamine cryptate (KNH$_2$) and the pyridine-bis-pyridine cryptate [Eu$^{3+}$ Cpy.Bpy.Bpy], the preparations of which have been described, respectively, in EP 0 321 353 and in Helv. Chim. Acta 1988, 71, 1042.

The formulae of these two molecules are given below:

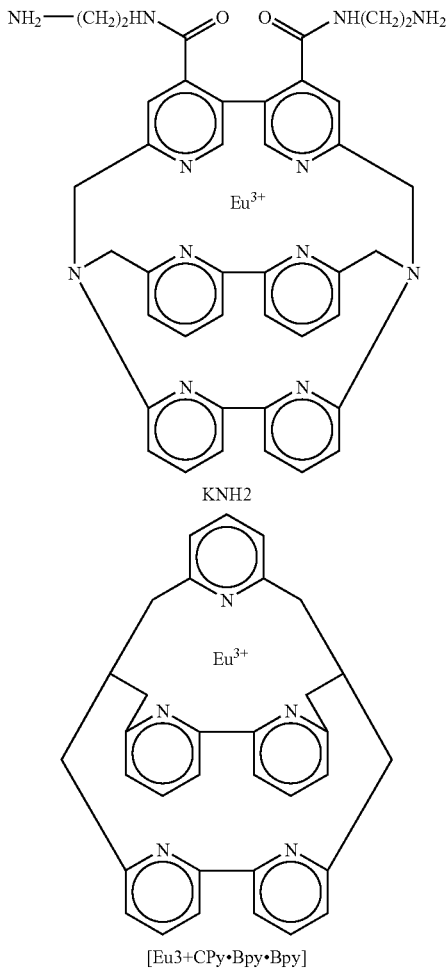

The results are given in Table 1 below:

TABLE 1

| Complexes tested | $\tau PO_4^{3-}$ buffer (ms) | $\tau$ serum (ms) | Quenching $1 - \left( \dfrac{\tau\text{-serum}}{\tau PO_4^{3-}} \right)$ % |
|---|---|---|---|
| KNH2 | 0.6 | 0.15 | 75% |
| Example 2 macrobicycle 6 | 1.06 | 0.80 | 25% |
| Example 4(b) macrobicycle 12 | 1.03 | 0.90 | 13% |
| Example 6 macrobicycle 19 | 1.03 | 0.90 | 13% |
| Example 7 macrobicycle 20 | 1.01 | 0.89 | 12% |
| Example 8 antibody-cryptate conjugate | 0.95 | 0.86 | 9.5% |
| [Eu3+ ⊂ Bpy.Bpy.py] | 0.66 | 0.54 | 18% |

These results show that, in a trisbipyridine cryptate structure, replacing a bipyridine unit with a pyridine unit has the effect of reducing the fluorescence quenching caused by the serum. These results also demonstrate that the presence of carboxylate groups on the bipyridine units has a favorable influence on reducing the quenching.

The invention claimed is:

1. A process for reducing the fluorescence quenching caused by the measuring medium in a fluorescence assay of an analyte using at least one fluorescent label, comprising introducing a rare earth metal macropolycyclic complex into the measuring medium, the complex comprising at least one rare earth metal ion complexed with a macropolycyclic compound of formula

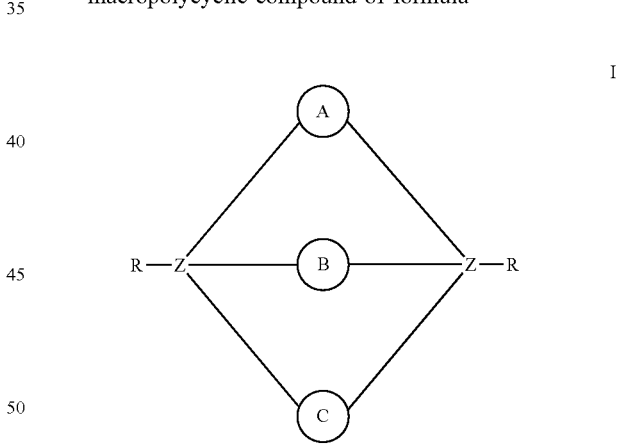

I in which

Z is an atom with 3 or 4 valencies,

R is absent or hydrogen, a hydroxyl group, an amino group or a hydrocarbon radical, Ⓐ, Ⓑ and Ⓒ are divalent radicals and are, independently of each other, a hydrocarbon chain optionally containing one or more heteroatoms and are optionally interrupted with a heteromacrocycle, wherein two of the radicals Ⓐ, Ⓑ and Ⓒ also comprise at least one molecular unit or consist essentially of a molecular unit having a triplet energy which is greater than that of the emission level of the complexed rare earth metal ion and which is substituted with an electron-donating group, and one of the radicals Ⓐ, Ⓑ and Ⓒ which does not comprise or does not consist essentially of the molecular unit having a triplet energy comprises only one pyridine radical which is substituted one or more times or unsubstituted, and measuring the fluorescent signal emitted in the assay.

2. The process as claimed in claim 1, wherein a molecular unit having a triplet energy which is greater than that of the emission level of the complexed rare earth metal ion is chosen from phenanthroline, anthracene, benzene, naphthalene, biphenyl, terphenyl, azobenzene, azopyridine, bipyridines and bisisoquinolines.

3. The process as claimed in claim 1, wherein a molecular unit having a triplet energy which is greater than that of the emission level of the complexed rare earth metal ion is a bipyridine group.

4. The process as claimed in claim 3, wherein the bipyridine group(s) is (are) substituted with an electron-donating group, carboxylate, $-NH_2$, $-NHAlk$, $-N(Alk)_2$, $OH$, $O^-$, $-OAlk$, $Alk$, $-CH(Alk)_2$, $-C(Alk)_3$, $-NHCOAlk$, and substituted and unsubstituted phenyl groups; Alk being a $(C_1-C_4)$alkyl group.

5. The process as claimed in claim 2, wherein the bipyridine unit(s) is (are) substituted with a carboxylate group.

6. The process as claimed in claim 1, wherein the macropolycyclic complex comprises at least one rare earth metal ion complexed with a macropolycyclic compound of formula II:

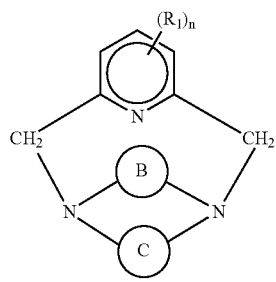

II in which:

the ring of formula

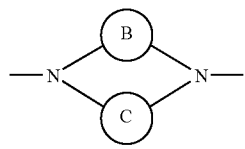

is the bis-bipyridine macrocycle of formula:

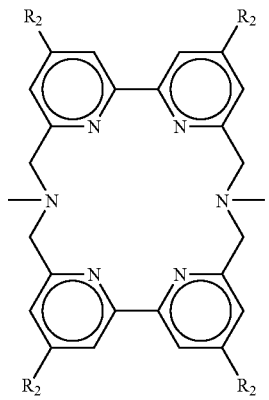

$-n=0$, 1 or 2;

$R_1$ is a group $-COOR_3$ in which $R_3$ is hydrogen or a $C_1$ to $C_{10}$ alkyl group or $R_1$ is a group $-CO-NH-Y-A$ or $-Y-A$;

$R_2$ is hydrogen, an electron-donating group, carboxylate, $-NH_2$, $-NHAlk$, $-N(Alk)_2$, $OH$, $O^-$, $-OAlk$, $Alk$, $-CH(Alk)_2$, $-C(Alk)_3$, $-NHCOAlk$, substituted or unsubstituted phenyl; Alk being a $(C_1-C_4)$alkyl group, or a group $-CO-NH-Y-A$ or $-Y-A$, with the proviso that not more than one of the substituents $R_1$ and $R_2$ represents a group $-CO-NH-Y-A$ or $-Y-A$ and $R_1$ and $R_2$ do not simultaneously represent a group $-CO-NH-YA$ or $-Y-A$;

A is a functional group capable of bonding covalently with a biological substance;

Y is a spacer group or spacer arm which consists of a divalent organic radical, chosen from linear or branched $C_1$ to $C_{20}$ alkylene groups optionally containing one or more double bonds and/or one or more heteroatoms, oxygen, nitrogen, sulfur or phosphorus or one or more carbamoyl or carboxamido group(s); or chosen from $C_5$ to $C_8$ cycloalkylene groups or from $C_6$ to $C_{14}$ arylene groups, the alkylene, cycloalkylene or arylene groups being optionally substituted with an alkyl, aryl or sulfonate group.

7. The process as claimed in claim 1, wherein the complexed rare earth metal ion is a europium ion.

8. The process as claimed in claim 1, wherein the rare earth metal macropolycyclic complex is chosen from the europium cryptates $[Eu^{3+} \subset py.bpy(CO_2H)_2.bpy(CO_2H)_2]$, $[Eu^{3+} \subset bpy(CO_2H)_2.bpy(CO_2H)_2.py(NH_2)_2]$ and $[Eu^{3+} \subset bpy(CO_2H)_2.bpy(CO_2H)_2.py(CONH(CH_2)_2NHR_4]_2$ in which

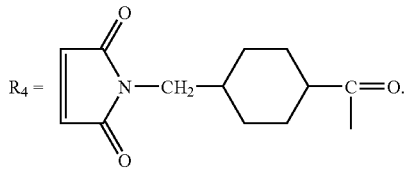

9. The process as claimed claim 1, wherein the rare earth metal macropolycyclic complex is used as sole label or as one of the labels in the assay.

10. The process as claimed in claim 1, wherein the measuring medium is a biological medium or a serum medium.

11. A rare earth metal macropolycyclic complex comprising at least one rare earth metal ion complexed with a macropolycyclic compound of formula

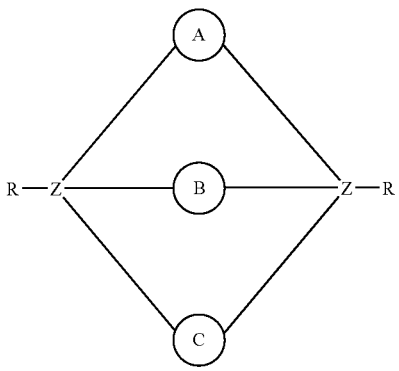

I in which

Z is an atom with 3 or 4 valencies,

R is absent or hydrogen, a hydroxyl group, an amino group or a hydrocarbon radical, Ⓐ, Ⓑ and Ⓒ divalent radicals and are, independently of each other, a hydrocarbon chain which optionally contain one or more heteroatoms and are optionally interrupted with a heteromacrocycle, two of the radicals Ⓐ, Ⓑ and Ⓒ also comprise at least one molecular unit or consist essentially of a molecular unit having a triplet energy which is greater than that of the emission level of the complexed rare earth metal ion and which is substituted with an electron-donating group, and one of the radicals Ⓐ, Ⓑ and Ⓒ which does not comprise or does not consist essentially of the molecular unit having a triplet energy comprises only one pyridine radical substituted one or more times.

12. The complex as claimed in claim 11, wherein the complexed rare earth metal ion is a europium ion.

13. The complex as claimed in claim 11, wherein a molecular unit having a triplet energy which is greater than that of the emission level of the complexed rare earth metal ion is chosen from phenanthroline, anthracene, benzene, naphthalene, biphenyl, terphenyl, azobenzene, azopyridine, bipyridines and bisisoquinolines.

14. The complex as claimed in claim 11, wherein a molecular unit having a triplet energy which is greater than that of the emission level of the complexed rare earth metal ion is a bipyridine group.

15. The complex as claimed in claim 14 wherein the bipyridine group(s) is (are) substituted with an electron-donating group, carboxylate, —NH$_2$, —NHAlk, —N(Alk)$_2$, OH, O$^-$, —OAlk, Alk, —CH(Alk)$_2$, —C(Alk)$_3$, —NHCOAlk, and substituted and unsubstituted phenyl groups; Alk being a (C$_1$–C$_4$)alkyl group.

16. The complex as claimed in claim 14, wherein the bipyridine unit(s) is (are) substituted with a carboxylate group.

17. The complex as claimed in claim 11, which comprises at least one rare earth metal ion complexed with a macropolycyclic compound of formula II:

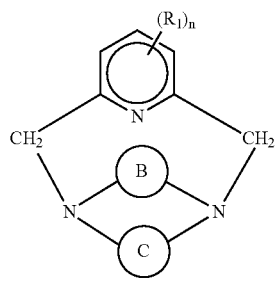

II in which:
the ring of formula

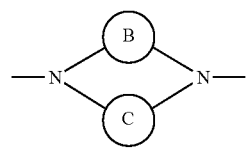

is the bis-bipyridine macrocycle of formula:

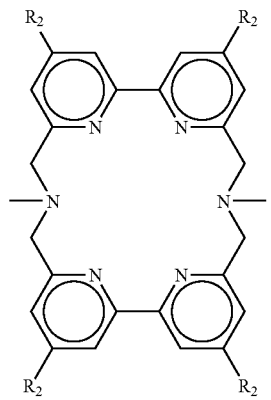

n=0, 1 or 2;

Y is a spacer group or spacer arm which consists of a divalent organic radical, chosen from linear or branched C$_1$ to C$_{20}$ alkylene groups optionally containing one or more double bonds and/or one or more heteroatoms, oxygen, nitrogen, sulfur or phosphorus or one or more carbamoyl or carboxamido group(s); or chosen from C$_5$ to C$_8$ cycloalkylene groups or from C$_6$ to C$_{14}$ arylene groups, the alkylene, cycloalkylene or arylene groups being optionally substituted with an alkyl, aryl or sulfonate group, R$_1$ is a group —COOR$_3$ in which R$_3$ is hydrogen or a C$_1$ to C$_{10}$ alkyl group or R$_1$ is a group —CO—NH—Y-A or —Y-A;

R$_2$ is hydrogen, an electron-donating group, carboxylate, —NH$_2$, —NHAlk, —N(Alk)$_2$, OH, O$^-$, —OAlk, Alk, —CH(Alk)$_2$, —C(Alk)$_3$, —NHCOAlk, substituted or unsubstituted phenyl; Alk being a (C$_1$–C$_4$)alkyl group or a group —CO—NH—Y-A or —Y-A, A is a functional group which can bond covalently with a biological substance; with the proviso that not more than one of the substituents R$_1$ and R$_2$ represents a group —CO—NH—Y-A or —Y-A and R$_1$ and R$_2$ do not simultaneously represent a group —CO—NH—Y-A or —Y-A, and with the proviso that when n=0, R$_2$ is other than hydrogen.

18. The complex as claimed in claim 17, which comprises at least one rare earth metal ion complexed with a macropolycyclic compound of formula II in which:

n=0,

Y, A and R$_1$ are as defined in claim 17, and

R$_2$ is as defined in claim 17 and one of the substituents R$_2$ is a group —CO—NH—Y-A or —Y-A.

19. The complex as claimed in claim 17, which is chosen from the europium cryptates [Eu$^{3+}$ ⊂ py.Bpy(CO$_2$H)$_2$.Bpy (CO$_2$H)$_2$], [Eu$^{3+}$ ⊂ bpy(CO$_2$H)$_2$.bpy(CO$_2$H)$_2$.py(NH$_2$)$_2$] and [Eu$^{3+}$ ⊂ bpy(CO$_2$H)$_2$.bpy(CO$_2$H)$_2$.py(CONH(CH$_2$)$_2$NHR$_4$]$_2$ in which

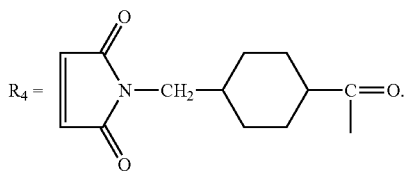

20. A fluorescent conjugate comprising a complex as claimed in claim 11 bonded covalently to one of the members of a pair of molecules capable of bonding together specifically.

21. In a fluorescence assay of an analyte using at least one rare earth metal cryptate as a fluorescent label, the improvement comprising replacing the rare earth cryptate with a macropolycyclic complex as claimed in claim 11 for reducing the fluorescence quenching caused by the measuring medium.

22. A fluorescent conjugate according to claim 20, wherein the one member of a pair of molecules to which the complex is bonded to is a polypeptide, a protein, a cell receptor, an antigen, an antibody or a nucleic acid.

* * * * *